(12) United States Patent
Abel et al.

(10) Patent No.: US 11,406,745 B2
(45) Date of Patent: Aug. 9, 2022

(54) BALANCING METHOD AND BALANCING UNIT BEING INDEPENDENT OF TEMPERATURE DISTURBANCE

(71) Applicant: Fresenius Medical Care Deutschland GmbH, Bad Homburg (DE)

(72) Inventors: Petra Abel, Friedberg (DE); Alexander Heide, Eppstein (DE); Dejan Nikolic, Frankfurt (DE); Arne Peters, Bad Homburg (DE); Elke Schulte, Schweinfurt (DE); Christoph Wiktor, Gelnhausen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 174 days.

(21) Appl. No.: 15/559,559

(22) PCT Filed: Mar. 21, 2016

(86) PCT No.: PCT/EP2016/056152
§ 371 (c)(1),
(2) Date: Sep. 19, 2017

(87) PCT Pub. No.: WO2016/150916
PCT Pub. Date: Sep. 29, 2016

(65) Prior Publication Data
US 2018/0043072 A1 Feb. 15, 2018

(30) Foreign Application Priority Data
Mar. 24, 2015 (DE) .......................... 102015104431.5

(51) Int. Cl.
*A61M 1/16* (2006.01)
*G01F 1/60* (2006.01)

(52) U.S. Cl.
CPC ........ *A61M 1/1647* (2014.02); *A61M 1/1635* (2014.02); *A61M 1/1662* (2014.02);
(Continued)

(58) Field of Classification Search
CPC .............. A61M 1/1605; A61M 1/1647; A61M 1/1613; A61M 1/1635; A61M 1/1662;
(Continued)

(56) References Cited

U.S. PATENT DOCUMENTS 4,267,040 A * 5/1981 Schal .................. A61M 1/1607
 210/104
4,404,638 A * 9/1983 Yada ....................... G01F 15/02
 377/21

(Continued)

FOREIGN PATENT DOCUMENTS

CN 103702695 4/2014
DE 2858204 10/1984
(Continued)

OTHER PUBLICATIONS

International Search Report in International Application No. PCT/EP2016/056152, dated Jun. 23, 2016, 6 pages (with English translation).
International Preliminary Report on Patentability in Application No. PCT/EP2016/056152, dated Sep. 26, 2017, 8 pages.

*Primary Examiner* — Justin N Olamit
(74) *Attorney, Agent, or Firm* — Fish & Richardson P.C.

(57) ABSTRACT

This disclosure relates to a method for determining a fluid balance between a first volume flow in a first section of a fluid circuit and a second volume flow of a second section of the fluid circuit. The method may also include adjusting, assuming or detecting a first temperature in the first section of the fluid circuit and a second temperature in the second section of the fluid circuit, or detecting a temperature difference between the first and the second sections. The (Continued)

method may also include detecting a second volume flow in a second section of the fluid circuit and forming a balance from at least the first volume flow and a corrected value of the second volume flow. The corrected value is determined from the detected second volume flow and the second temperature and/or the temperature difference.

7 Claims, 5 Drawing Sheets

(52) U.S. Cl.
CPC ............. *A61M 1/1664* (2014.02); *G01F 1/60* (2013.01); *A61M 2205/127* (2013.01); *A61M 2205/3317* (2013.01); *A61M 2205/3334* (2013.01); *A61M 2205/3372* (2013.01); *A61M 2205/366* (2013.01)

(58) Field of Classification Search
CPC .......... A61M 1/1664; A61M 2205/127; A61M 2205/3317; A61M 2205/3334; A61M 2205/3372; A61M 2205/366; G01F 1/60
See application file for complete search history.

(56) References Cited

U.S. PATENT DOCUMENTS

| | | | | |
|---|---|---|---|---|
| 4,530,759 | A | | 7/1985 | Schael |
| 4,720,800 | A | * | 1/1988 | Suzuki ................. G01F 15/024 377/21 |
| 8,105,260 | B2 | * | 1/2012 | Tonelli .................... A61M 1/16 210/645 |
| 8,915,876 | B2 | | 12/2014 | Gronau et al. |
| 9,568,346 | B2 | * | 2/2017 | Ramseyer ............... G01F 1/584 |
| 9,752,906 | B2 | | 9/2017 | Suzuki |
| 2012/0330214 | A1 | * | 12/2012 | Peters ................. A61M 1/1603 604/6.11 |

FOREIGN PATENT DOCUMENTS

| | | |
|---|---|---|
| DE | 19814695 | 10/1999 |
| DE | 102010003642 | 9/2011 |
| DE | 102012009043 | 11/2013 |
| EP | 715859 | 6/1996 |
| EP | 2532999 | 12/2012 |
| JP | S 55-059816 | 5/1980 |
| WO | WO 2013/175547 | 11/2013 |
| WO | 2016150916 | 9/2016 |

* cited by examiner

BALANCING METHOD AND BALANCING UNIT BEING INDEPENDENT OF TEMPERATURE DISTURBANCE

CROSS REFERENCE RELATED APPLICATIONS

The present application is a national stage entry of International Patent Application No. PCT/EP2016/056152, filed on Mar. 21, 2016, and claims priority to Application No. 10 2015 104 431.5, filed in on Mar. 24, 2015. The disclosures of the prior applications are expressly incorporated herein in entirety by reference thereto.

TECHNICAL FIELD

This disclosure relates to a method for balancing fluids flows and/or for controlling or regulating at least one volume flow. This disclosure also relates to a medical functional device, a balancing unit, a medical treatment apparatus, a digital storage medium, a computer program product and a computer program.

BACKGROUND

In medicine, in particular in the field of blood treatment, for example of dialysis, the patient is supplied with fluids and/or fluids are withdrawn from the patient. The exact balancing of the quantity of the fluids supplied and withdrawn is of essential importance for the safety and health of the patient.

Balancing units are used in practice to achieve the balance. They may be connected to blood treatment apparatuses, for example dialysis apparatuses.

During an extracorporeal blood treatment, heater or heating units are regularly used, for example to compensate for heat losses of blood outside the body. This may cause a complex temperature evolution of the liquids used in the extracorporeal blood circuit, and also in the remaining fluid circuit. Thus, the fluids used or supplied for the extracorporeal circuit(s) may have different temperatures from each other. Due to the fact that temperatures may have an influence on the volume of the fluid(s), the temperature may influence not only the volume, but also the balancing. Stated another way, the balancing may be inaccurate when the influence of the temperature on the volume is not considered.

SUMMARY

In one aspect, this disclosure relates to a method for the determination of a fluid balance between a first volume flow in a first section of a fluid circuit of a functional device, and a second volume flow in a second section of the fluid circuit of the functional device.

The method relates alternatively or additionally to the control and/or regulation (for better readability, both terms are referred to as "controlling", which however optionally also encompasses regulating) of at least one volume flow of at least one section of the fluid circuit of the functional device.

The method encompasses at least the step of determining (e.g., adjusting, setting, estimating, obtaining, detecting and/or assuming) at least one first volume flow in at least one first section of the fluid circuit. The method encompasses further at least the step of determining (e.g., adjusting, setting, estimating, obtaining, assuming or detecting) at least one first temperature in the at least one first section of the fluid circuit.

The method further encompasses at least the step of determining (e.g., adjusting, setting, estimating, obtaining, detecting and/or assuming) at least one second temperature in at least one second section of the fluid circuit, or of determining (e.g., adjusting, setting, estimating, obtaining, detecting and/or assuming) at least one temperature difference between the first and the second sections of the fluid circuit.

The method further encompasses at least the step of determining (e.g., adjusting, setting, estimating, obtaining, detecting and/or assuming) at least one second volume flow in the at least one second section of the fluid circuit.

In addition, the method encompasses at least determining, (e.g., calculating, estimating, building, or forming) a fluid balance from at least the first volume flow and a corrected value of the second volume flow. The corrected value F2_korr is determined and/or calculated at least from the second volume flow and the second temperature and/or the temperature difference between the first and the second sections of the fluid circuit.

A functional device, which is preferably a medical functional device, is also described herein. It comprises at least one fluid circuit, or at least one section thereof, or is connected and/or connectable therewith. It further comprises at least one flow sensor. Alternatively, it is configured and/or embodied to be detachably, connected or connectable with a flow sensor.

Thereby, the flow sensor is embodied and/or arranged for the measurement of, or for measuring, at least one volume flow in at least one section, in particular in one first and/or in one second section of the fluid circuit.

The functional device further comprises at least one device for detecting a temperature and/or a temperature difference in at least one section of the fluid circuit. Such a device may be included, arranged and/or embodied in at least one section of the fluid circuit, in particular in a first and/or a second section. Such a device may be provided and/or embodied to measure the temperature of at least a fluid flowing through a section, or of the fluid present therein, and/or to measure the temperature of the respective sections.

A balancing unit described herein is provided and/or embodied for the determination of at least one fluid balance, in particular a fluid balance between at least one (or exactly one) first fluid flow in or through a first section of a fluid circuit and one second volume flow in or through a second section of the fluid circuit.

The balancing unit comprises for this purpose at least one functional device. Alternatively or additionally thereto, the balancing unit may be in data communication with at least one device for detecting the temperature, the temperature difference, and/or the volume flow of the fluid circuit, or with at least one flow sensor and/or at least one pump, for example a blood pump.

Alternatively or additionally, the balancing unit is embodied and/or configured to execute the methods described herein.

A medical treatment apparatus described herein, which is embodied and/or configured for the treatment of a medical fluid, comprises at least one balancing unit as described herein and/or at least one functional device as described herein, and/or it is at least embodied and/or configured for executing the method.

A digital, particularly a non-volatile storage medium, particularly as a machine-readable data storage device, particularly as a disk, CD, EPROM or DVD, with electrically readable control signals, may interact with a programmable computer system such that the mechanical steps of the methods described herein are prompted. Thereby, all or some of the machine-induced steps of the methods described herein may be prompted.

A computer program product as described herein comprises a program code that is volatile or saved on a machine-readable medium for prompting the mechanical steps of the methods described herein when the computer program product runs on a computer. Such a computer program product can be understood as, for example, a computer program which is stored on a storage device, an embedded system as a comprehensive system with a computer program (e.g. an electronic device with a computer program), a network of computer-implemented computer programs (e.g. a client-server system, a cloud computing system, etc.), or a computer on which a computer product is loaded, executed, saved or developed.

The term machine-readable medium as used herein denotes, in certain embodiments, a medium containing data or information which is interpretable by software and/or hardware. The medium may be a data medium, like a disk, a CD, a DVD, an USB stick, a flashcard, an SD card or the like.

A computer program as used herein comprises a program code for prompting the mechanical steps of a method when the computer program runs on a computer. A computer program can be understood as, for example, a physical, ready-for-distribution software product which comprises a computer program.

It also applies for the computer program product and the computer program that all or some of the mechanically executed steps of the methods described herein are prompted.

Embodiments as described herein may comprise some or all of the following features in any combination.

In all of the previous and following embodiments, the use of the expression "may be" or "may have" and so on, is to be understood synonymously with "preferably is" or "preferably has," respectively, and so on, and is intended to illustrate embodiments.

Embodiments may exhibit some or all of the following features in any combination, provided it is not obviously technically impossible for those skilled in the art.

Whenever a numerical value is mentioned herein, the person skilled in the art understands it as an indication of a numerical lower limit. Unless it leads the person skilled in the art to an evident contradiction, the skilled person implicitly understands when specifying for example "one" always as "at least one". This understanding is also evenhandedly encompassed by some embodiments as the interpretation that a numeric word, for example, "one" may alternatively mean "exactly one", wherever this is not evidently technically impossible for the skilled person. Both are encompassed in some embodiments and apply herein to all used numerical values.

Spatial indications made herein such as "top", "bottom", etc. refer in case of doubt to the illustrations as can be seen in the accompanying figures.

Whenever the expression "suitable", "provided", "designed", "configured" and/or "programmed", are used herein, a person skilled in the art may understand a particular embodiment of the respective apparatus. The aforementioned expressions may be used herein interchangeably.

Although the present invention is described hereinafter primarily with reference to a dialysis treatment, the present invention is not limited thereto.

The expression "volume flow", as used herein, may be understood to refer to a volumetric flow rate. That is, "volume flow" may be understood as the volume of a fluid which has moved or streamed or flowed within a given period of time through a cross-section (e.g. a cross-section of a portion of the fluid circuit) with respect to the corresponding given period of time. A volume flow may be exemplarily specified in ml per minute or per hour.

The expression "mass flow", as used herein, may be equal to the density of the fluid multiplied by the volume flow.

The expression "determining", as used herein, includes actions such as, but not limited to, adjusting, setting, estimating, obtaining, detecting, assuming, measuring, identifying, and reading or capturing (for example of a stored and/or set or adjusted value and/or a calculation, in particular from known, stored, determined and/or preset or adjusted values).

In some exemplary embodiments, the method is executed in interaction with a functional device described herein, a balancing unit described herein and/or a blood treatment apparatus described herein.

In some exemplary embodiments, the method encompasses at least adjusting or assuming at least one temperature in at least one section of the fluid circuit. It encompasses in these embodiments preferably at least adjusting at least one volume flow in at least one section of the fluid circuit.

"Assuming a temperature", may be understood as the estimation of the temperature or the setting or adjusting of a temperature value for further consideration. This may for example take place when the value of the temperature can be concluded from values based on experience values, for example based on the temperature which the fluid has in or when leaving a fluid source.

"Adjusting or setting a temperature" may be understood as changing the temperature or for example changing the temperature by means of a regulator, heater, etc.

In some exemplary embodiments, at least the values of the adjusted or set volume flow and/or the adjusted or set temperature are determined, at least temporarily stored, or saved.

In certain exemplary embodiments, a method step comprises at least the adjustment of a volume flow in a section of the fluid circuit, e.g. a first volume flow in a first section, in particular prior to the formation of the fluid balance.

With "at least one volume flow" or respectively "at least one temperature", it may be understood herein as for example the first and/or the second volume flow, i.e. the volume flow of the first and/or the second section, or respectively the first and/or the second temperature, i.e. the temperature of the first and/or of the second volume flow.

In some exemplary embodiments, the fluid balance (here abbreviated as FB), the corrected value of the volume flow $F2\_korr$, the temperature $T1$, $T1'$ or the temperature difference $DT$ may be used as signal, and/or for generating a signal, for a control and/or regulating device for controlling and/or regulating at least one volume flow of the fluid circuit, a pump rate of at least one pump of the fluid circuit, a cross section of at least one section of the fluid circuit and/or a temperature, for example by means of a heater, in the fluid circuit.

In some particular exemplary embodiments, a fluid balance FB is formed or determined based on at least one first volume flow $F1$ and one second volume flow $F2$. For example, in some exemplary embodiments the fluid balance FB may be formed or determined as follows:

$$FB=F1-F2, \text{ or} \quad \text{(Formula 1)}$$

$$FB=F2-F1. \quad \text{(Formula 1')}$$

In some exemplary embodiments, a fluid balance FB is formed or determined based on at least one first volume flow F1 or F2 and one corrected value of a second volume flow F2_korr or F1_korr. As used herein, "corrected" means adjusted to compensate for differences in the temperatures of the fluids (for example temperature differences between F1 and F2). For example, in some exemplary embodiments, the fluid balance FB is formed or determined as follows:

$$FB=F1-F2\_korr, \text{ or} \quad \text{(Formula 2)}$$

$$FB=F2\_korr-F1, \text{ or} \quad \text{(Formula 2')}$$

$$FB=F2-F1\_korr, \text{ or} \quad \text{(Formula 2'')}$$

$$FB=F1\_korr-F2. \quad \text{(Formula 2''')}$$

In some exemplary embodiments, the corrected volume flow (flow value F2_korr or flow value F1_korr) is determined or calculated at least from one detected volume flow F1 or F2 and one detected temperature T1, T1', T2, and/or T2'. For example, in some exemplary embodiments, the corrected value Fi_korr, (with i=1 or 2) may be formed or determined as follows:

$$Fi\_korr=Fi*(1+K*(T1-T2)), \text{ or} \quad \text{(Formula 3)}$$

$$Fi\_korr=Fi*(1+K*(T2-T1)), \quad \text{(Formula 3')}$$

wherein K is a correction factor.

The correction factor K can be predetermined. It may be determined experimentally or theoretically. It may be stored and thereby available for the calculations described herein. It may exemplarily comprise the unit $[° C.^{-1}]$. It can be negative or positive. T1 and/or T2 are optionally measured, determined, adjusted, set or identified temperature values of the fluid in the respective sections of the fluid circuit.

In some exemplary embodiments, the corrected volume flow (flow value Fi_korr) is determined and/or calculated while taking into account the temperature difference DT between two different sections of the fluid circuit.

In some exemplary embodiments, the corrected volume flow of flow value Fi_korr is obtained from a look-up table, in which this value corresponds to the temperature difference (DT).

In some exemplary embodiments, the corrected value (Fi_korr) is formed as follows:

$$Fi\_korr=Fi*(1+K*(DT)), \text{ with } i=1 \text{ or } 2. \quad \text{(Formula 4)}$$

In some exemplary embodiments, the corrected value (Fi korr) and/or a corrected pump rate or fluid rate (or a corrected control signal for one of the pumps, e.g. for the ultrafiltration pump) is determined and/or calculated at least from one, preferably stored or readable, temperature-dependent physical quantity of the fluid in the fluid circuit, for example its density, and/or at least from one predetermined, stored, readable, or previously determined, factor K.

In some exemplary embodiments, a corrected ultrafiltration rate (UF_korr), based at least on the temperature difference (DT) between two volume flows, may be determined as follows;

$$UF\_korr=UF+F1*K+DT. \quad \text{(Formula 5)}$$

UF is thereby the previously adjusted or set ultrafiltration rate before correction.

In some exemplary embodiments, stored values, for example values indicating the density of the relevant fluid at certain temperatures, may be saved or stored and read. Such values are used in these embodiments for calculating the fluid balance or another value, for example a corrected ultrafiltration rate.

In some exemplary embodiments, the fluid balance (FB) and/or the corrected ultrafiltration rate is used as a signal and/or for generating a signal for the control device for controlling or regulating at least one volume flow of the fluid circuit.

In some exemplary embodiments, the first or the second volume flow may be in particular increased or decreased.

A correction may in some exemplary embodiments be based directly on electrical measurement values or readings. For this, the signals which are to be generated out of the received evaluation values, are suitably corrected.

In some exemplary embodiments, a volume flow is controlled and/or regulated in the fluid circuit or into a connected circuit through a change and/or an adjustment of a pump rate of at least one pump, in particular of the fluid circuit or of a therewith connected circuit, a cross section of at least one section and/or a temperature, for example by a heater.

In some exemplary embodiments, the device for detecting at least one temperature difference may be arranged and/or embodied between two different sections of the fluid circuit, in particular between the first and the second section, or determines and/or measures at least the temperature difference between these two sections.

In some exemplary embodiments, the functional device and/or at least one section of the fluid circuit is provided and/or embodied to be connectable and/or connected and/or to get connected to at least one section of at least one flow sensor, for example a measuring section, preferably in a detachable, e.g. interchangeable manner. In certain exemplary embodiments, such a connection is provided.

In some exemplary embodiments, a "section of the fluid circuit" may be understood in particular as the first section or the second section of the fluid circuit, in particular of the dialysate and/or substituate circuit.

A "volume flow of the fluid circuit", may be understood, in certain exemplary embodiments, in particular as the volume flow of the first section or the volume flow of the second section of the fluid circuit, in particular of the dialysate and/or substituate circuit.

In some exemplary embodiments, the functional device, in particular the medical or medical technical functional device, comprises at least one fluid circuit, in particular a process fluid circuit, for example a liquid circuit, or sections thereof.

The expression "fluid circuit", as used herein, denotes a fluid system, a tube set, a blood tubing set or the like, each adequate, intended and/or designed to receive and be flowed through by, process fluids, medical liquids, e.g. blood, substituate, dialysate and/or combinations thereof. The process fluids may be used for the purpose of a process such as flushing, priming, substituting, decreasing or lowering the concentration of pollutants and the like. In some examples, a fluid circuit may not form or enable a closed circuit. A fluid circuit may comprise at least one filter device, e.g. a blood filter, and/or at least one pump, e.g. a blood and/or a substituate pump.

In some exemplary embodiments, the fluid circuit or at least a section thereof is provided and/or embodied to receive and/or to convey at least one fluid, in particular a medical fluid.

In some exemplary embodiments, the functional device comprises at least one channel which is at least suitable or adequate and/or embodied to convey and/or to lead a liquid.

In some exemplary embodiments, the fluid circuit is an arterial and/or venous, blood, dialysate and/or substituate circuit.

The functional device may further comprise at least one filter device, wherein the functional device is arranged inside the fluid circuit, in particular between a blood circuit and at least one dialysate circuit, or at least one section thereof. The filter device can be a blood filter or a dialyzer.

In some exemplary embodiments, at least one section of the flow sensor, preferably at least one measurement section thereof, is integrated and/or integrally embodied in the functional device and/or in the fluid circuit or in at least one section thereof.

In some exemplary embodiments, the flow sensor for detecting at least one volume flow is embodied in or at least two, preferably different sections of the fluid circuit, respectively.

In some exemplary embodiments, the first section, in an operating state of the functional device, is located upstream of a filter device, for example a blood filter, in particular with respect to a flow direction of the fluid during the operation of the functional device, for example during a treatment. Alternatively or additionally, the second section, in an operating state of the functional device, downstream of a filter device, for example a blood filter, is located with respect to a flow direction of the fluid during the operation of the functional device, for example during a treatment.

In some exemplary embodiments, the functional device and/or the fluid circuit may comprise at least one heat exchange device or be connected therewith.

In some exemplary embodiments, the heat exchange device may be arranged and/or embodied at least between two different sections of the fluid circuit, in particular between the first section and the second section.

In some exemplary embodiments, the heat exchange device may be dimensioned and arranged such that the difference between the temperature of the fluid flowing through the first section of the fluid circuit and the temperature of the fluid flowing through the second section of the fluid circuit is at least reduced, balanced, substantially equal or identical, within a pre-determinable, pre-defined, adjustable and/or pre-definable, at least limited or pre-determined time.

Alternatively or additionally, the temperature difference between fluids flowing in the relevant sections and/or the respective sections, before and after leaving the heat exchange device, may in some exemplary embodiments, be reduced, for example, by about at least 10%, 20%, 30%, 40%, 50%, 60% or more.

In some exemplary embodiments, the heat exchange device is arranged and/or embodied in at least one section of the fluid circuit before at least one flow sensor in the fluid circuit, with respect to the flow direction of the fluid in a direction through the heat exchange device (i.e. upstream to the flow sensor).

In some exemplary embodiments, the fluid circuit and/or the heat exchange device comprise at least one heater.

In certain exemplary embodiments, a heater is arranged during operation before or at or after the heat exchange device, a flow sensor or a filter device, with respect to the flow direction of the fluid.

In some exemplary embodiments, at least one section of at least one flow sensor and/or at least one section of the fluid circuit, in particular a first and/or a second section, for example a measuring section of the flow sensor, extends through at least one section of the heat exchange device, or is present therein.

In some exemplary embodiments, at least one section of the flow sensor and/or at least one section of the fluid circuit is embodied as a channel inserted in the functional device and/or in at least a heat-conducting body thereof, wherein the channel is preferably a closed channel in cross section or as a non-closed channel, for instance a half-channel or part-channel.

In some exemplary embodiments, at least one channel or part-channel may be sealed against an outside and/or against a further channel by a layer, in particular a heat-conductive and/or fluid-tight layer, for example a film and/or a thin plate and/or by another further channel.

In some exemplary embodiments, the functional device, the balancing unit and/or the treatment apparatus comprises at least one evaluation unit or evaluation device for determining at least one fluid balance between at least two sections of the fluid circuit, or is connected thereto by a data or signal communication.

In some exemplary embodiments, at least the functional device, the balancing unit or the treatment apparatus comprises at least one control and/or regulating device (hereinafter denoted for simplification as control device, although it may as well be a regulating device) for controlling and/or regulating (hereinafter denoted as "controlling") at least one volume flow in at least one section of the fluid circuit.

In some exemplary embodiments, the control device is embodied as a regulating device.

In some exemplary embodiments, the volume flow being controlled by the control device may be in particular a volume flow of a further section of the fluid circuit, for example the volume flow which flows through the filter device. The volume flow may exemplarily be an ultrafiltration rate.

In some exemplary embodiments, regulation and/or control of the volume flow is carried out at least on the basis of and/or at least by evaluating the fluid balance, the corrected value of the volume flow (F2_korr, F1_korr), the temperature or the temperature difference.

In some exemplary embodiments, at least the evaluation device and the control device form a unit.

In some exemplary embodiments, at least the functional device, the balancing unit, or the treatment apparatus comprises at least one flow sensor or is at least in data communication therewith.

In some exemplary embodiments, the evaluation device and/or the control device are at least in data communication with at least one flow sensor, at least one temperature sensor, and/or at least one treatment apparatus and/or with at least sections thereof respectively.

In some exemplary embodiments, the flow sensor or at least one section thereof, is an electromagnetic flow sensor, in particular a magnetic-inductive flow sensor (hereinafter also denoted shortly as "MID flow sensor") or it comprises such a one.

In some exemplary embodiments, at least one flow sensor is an at least two-channel flow sensor or comprises at least such a one.

In some exemplary embodiments, the functional device and/or a balancing unit is embodied as a tubing system, tubing set, cassette, in particular as a blood cassette.

In some exemplary embodiments, the functional device and/or the balancing unit is embodied as a single-use article or a disposable.

The expression "single-use article or disposable" as used herein may be understood so that the medical functional device is intended for single use, for example in a method for the extracorporeal blood treatment of a patient. The functional device may be provided and/or marketed as a disposable, single-use article, one-way article or the like.

In some exemplary embodiments, the balancing takes place in a blood treatment apparatus or during a blood treatment. This is not the case in some other embodiments.

In some exemplary embodiments, the control and/or regulating device of the treatment apparatus is in signal communication with the balancing unit. It is configured and/or programmed for executing at least one embodiment of the method, preferably in connection with the required devices.

In some embodiments, the balancing unit comprises at least one functional device or is at least connected and/or connectable with a functional device, such that the balancing unit and the functional device are in data communication.

In some exemplary embodiments, the balancing unit or the functional device or a treatment apparatus comprises at least one evaluation unit for forming at least one fluid balance between at least two volume flows in different sections of the fluid circuit.

In some exemplary embodiments, the balancing unit and/or the functional device and/or the treatment apparatus comprises at least one evaluation unit for determining at least one fluid balance between at least two sections of the fluid circuit. Alternatively or additionally, at least the balancing unit, the functional device or the treatment apparatus may comprise a control and/or regulating device for controlling and/or regulating at least one volume flow of the fluid circuit.

In some exemplary embodiments, the evaluation device and/or the control device is not embodied or arranged at or on the functional device, but may rather for example be part of the balancing unit or of the treatment apparatus and/or be arranged at a treatment apparatus.

Some or all of the respective control and/or regulating devices of the treatment apparatus, of the balancing unit, and/or of the functional device may comprise corresponding devices, in particular for executing the method and/or for controlling and/or regulating blood pumps, ultrafiltration pumps, or the like. The corresponding regulating and/or control devices may alternatively or additionally be at least in signal communication with these devices, respectively.

In some exemplary embodiments, the medical treatment apparatus is a blood treatment apparatus, in particular a blood cleaning apparatus such as hemofiltration apparatus, a hemodialysis apparatus, a hemodiafiltration apparatus, and/or a dialysis apparatus, for example an apparatus for acute dialysis, for home dialysis or peritoneal dialysis. It may be an apparatus for executing a method for liver replacement, an apparatus for executing immunoadsorption or the like.

In some exemplary embodiments, the functional device, the balancing unit and/or the treatment apparatus does not comprise any scale of balance or weighting device and/or balance chamber, in particular any non-ideal, rigid balance chamber.

In some exemplary embodiments, the method does not have gravimetric monitoring and/or the ultrafiltration rate is not directly measured with a sensor, and/or in particular is not measured with a MID sensor.

In some exemplary embodiments, the functional device does not comprise a blood container for the extracorporeal, temporal storage, and/or preferably does not comprise a blood container comprising a cylindrical body.

In some exemplary embodiments, the functional device does not comprise an air separator.

In some exemplary embodiments, the functional device does not comprise a temperature control element which can be integrated into the air separator.

In some exemplary embodiments, the functional device does not comprise a Peltier element.

In some exemplary embodiments, the functional device does not comprise a conveying device or devices, in particular the functional device does not comprise pump chambers.

In some exemplary embodiments, the functional device does not comprise a flow-through heater, in particular the functional device does not comprise a plurality of flow-through heaters.

In some exemplary embodiments, the functional device does not comprise a temperature control system, in particular the functional device does not comprise an electronic control for controlling temperature.

Some or all embodiments as described herein, may comprise one, several or all of the aforementioned features, and/or the following advantages.

All or some of the advantages achievable with the method can be achieved undiminished in certain embodiments, also with the functional device, the balancing unit, as well as with the medical treatment apparatus.

In some embodiments, a precise balancing is advantageously achieved or made possible.

The balancing may advantageously take place while simultaneously saving space and costs.

Measurements made with MID-flow sensors are measurements of a volume flow. The density of the fluid is temperature dependent. Thus, the volume flow, as well as a thereto corresponding mass flow, are temperature-dependent. In some particular embodiments however, a balancing which is advantageously independent of the influence of the temperature on the fluid to be balanced is advantageously achieved.

Furthermore, errors resulting from a temperature-dependent, geometrical and/or volumetric change of the used sensors are advantageously avoided.

In some embodiments, temperature-dependent errors, in particular geometry and/or density errors, are advantageously compensated.

In certain embodiments, errors in the balancing caused by temperature differences may be reduced at least by the factor 10 or more by.

In some exemplary embodiments, the measurement of the ultrafiltration rate is advantageously avoided, as a result of which a measurement sensor for measuring the ultrafiltration rate is dispensed with.

In some embodiments, in particular in embodiments of the functional device and/or of the heat exchange device as a single-use article, a microbial growth between successive treatments can be interrupted. Furthermore, infection risk between patients using the same blood treatment apparatus may be reduced, without involving or requiring particular measures/provisions or procedures for the disinfection.

Some embodiments can advantageously be dispensed with at least one temperature sensor or with all temperature sensors. The method can equally be executed with one temperature sensor or without any temperature sensor.

Another advantage of some embodiments may be to provide a further balancing method for balancing fluid flows and a further balancing device. In addition, an advantageous medical functional device, a medical treatment apparatus, a digital storage medium, a computer program as well a computer program product are disclosed.

In the figures, identical reference numerals denote the same, identical or similar components. The following applies:

DETAILED DESCRIPTION

Figure 1:
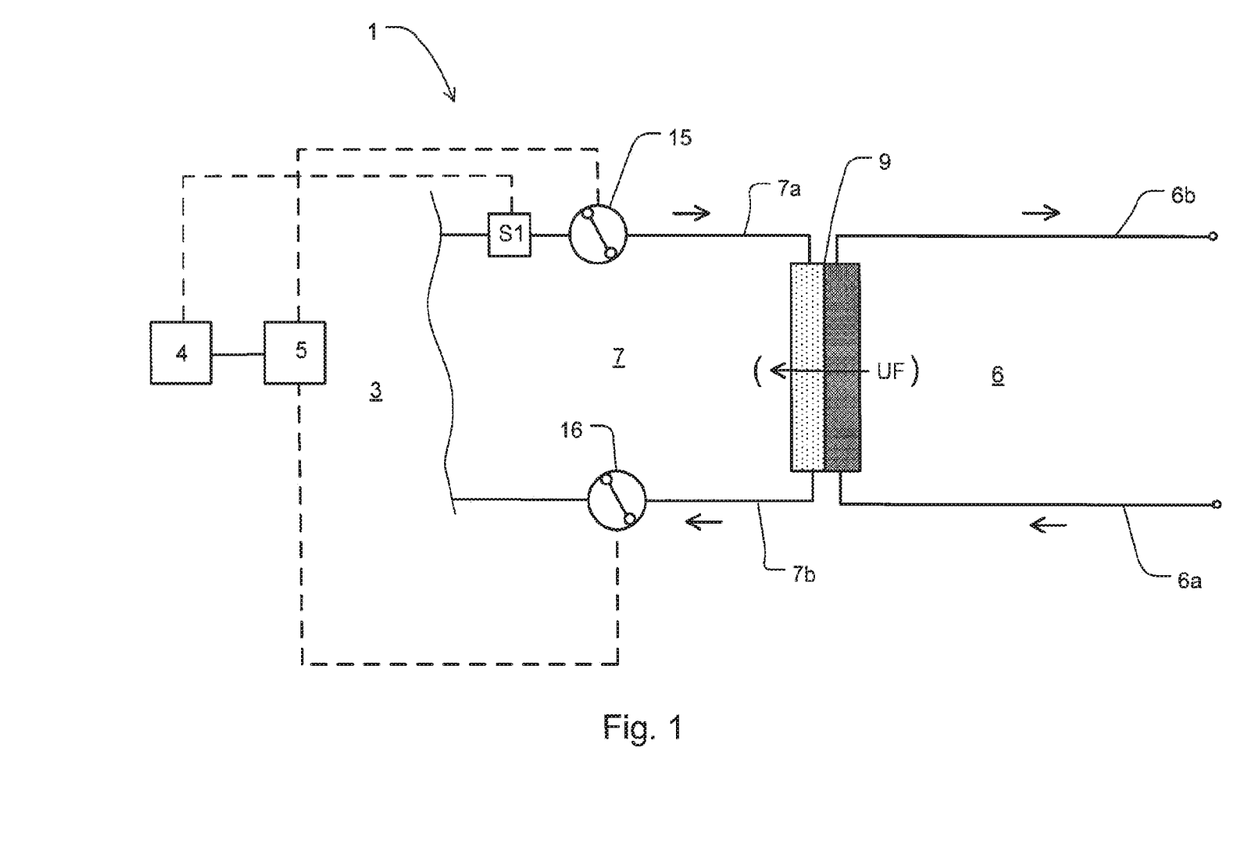
FIG. 1 shows, in a simplified illustration, a fluid circuit of an exemplary treatment apparatus.

FIG. 1 shows, in a highly simplified illustration, a section of a fluid circuit 1 which is connected in fluid communication with a roughly sketched or suggested treatment apparatus 3, or is, at least in section, part of the treatment apparatus 3. The treatment apparatus 3 is connected to a balancing unit 4 or comprises the latter. The treatment apparatus 3 is in addition connected to or comprises a control or regulating device 5 for controlling or regulating pumps, valves, etc. for the purpose of performing the treatment of the patient.

The balancing unit 4 is at least in data communication with a device S1 for detecting the temperature.

The balancing unit 4 may be part of the control or regulating device 5 of the treatment apparatus 3, or may be in signal communication with the former, as exemplarily depicted in FIG. 1.

The treatment device 3 illustrated in FIG. 1 and in all the following figures is purely exemplarily embodied as an ultrafiltration device; the fluid circuit 1 as a circuit for the extracorporeal blood treatment. Both of these assumptions serve solely for the better understanding of the present inventions with respect to a concrete example and should in no way limit the present inventions.

The fluid circuit 1 comprises an extracorporeal blood circuit 6 and a dialysate circuit 7, which, purely exemplarily, are in both substance and fluid exchange with each other by means of a filter or filtering device 9. The arrows denote a flow direction of different fluids during a treatment of a patient (not illustrated) by the treatment apparatus 3.

Blood of the patient flows in the extracorporeal blood circuit 6 through an arterial blood line 6a to the filter device 9 to be cleaned there. The cleaned blood is returned to the patient through a venous blood line 6b.

In the dialysate circuit 7, which may be a substituate or dialysate circuit, and which comprises a dialysis fluid line 7a and a dialysate line 7b, a first pump 15 and a second pump 16 are, for simplification, disposed or arranged for generating a particular volume flow in the dialysate circuit 7. They are, as suggested by the dashed line, each in signal communication with the control or regulating device 5.

Also the blood circuit 6 comprises preferably at least one pump (not illustrated in the figures) for conveying blood.

In FIG. 1, an arrow indicates an ultrafiltration occurring purely optionally, in which fluid from the blood circuit 6 enters with a flow or volume flow UF (ultrafiltration rate) through the filter 9 into the dialysate circuit 7. The ultrafiltration rate UF may be set by means of the control or regulating device 5 and respective pumps, e.g. the first pump 15, and/or the second pump 16.

The arrangement of FIG. 1 is adequate/suitable to execute the methods described herein due to the respectively programmed balancing unit 4 and/or to the respectively programmed control or regulating device 5.

The pumps 15, 16, illustrated in FIG. 1 are for the sake of simplicity not repeatedly illustrated in the following figures. They may however be provided unchanged in the following described embodiments.

Figure 2:
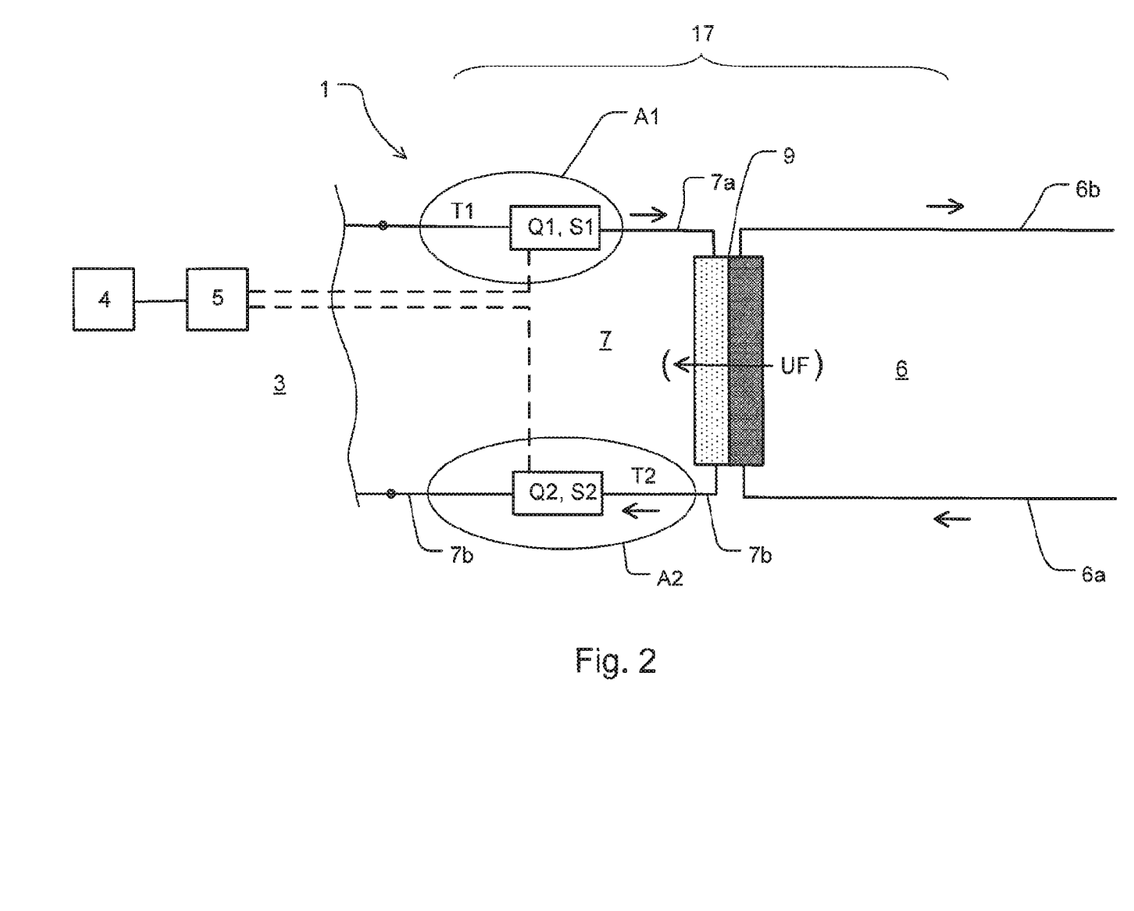
FIG. 2 shows, in a highly simplified illustration, an exemplary functional device having two flow sensors.

FIG. 2 shows, in a highly simplified illustration, a functional device 17, which comprises parts of the dialysate circuit 7 and, purely optionally, also parts of the blood circuit 6. The functional device 17 does not usually comprise the filter 9; it may however be connected or be connectable in fluid communication therewith.

In a first section A1 of the dialysate circuit 7, the latter comprises a first flow sensor Q1 or is connected therewith. In a second section A2 the dialysate circuit 7 comprises at least a second flow sensor Q2 or is connected therewith. The first and/or the second flow sensor Q1, Q2 is optionally part of the functional device 17, the balancing unit 4 or the treatment apparatus 3.

The first section A1 is exemplarily disposed in the dialysis fluid line 7a, the second section A2 is exemplarily disposed in the dialysate line 7b.

The temperature of the fluid entering or flowing into the first section A1 shall be denoted as T1.

The temperature of the fluid which flows out from the second section A2 shall be denoted as T2'. The second section A2 is optionally disposed downstream of the filter device 9.

The temperature of the fluid which enters or flows into the second section A2 shall be denoted as T2.

Figure 3:
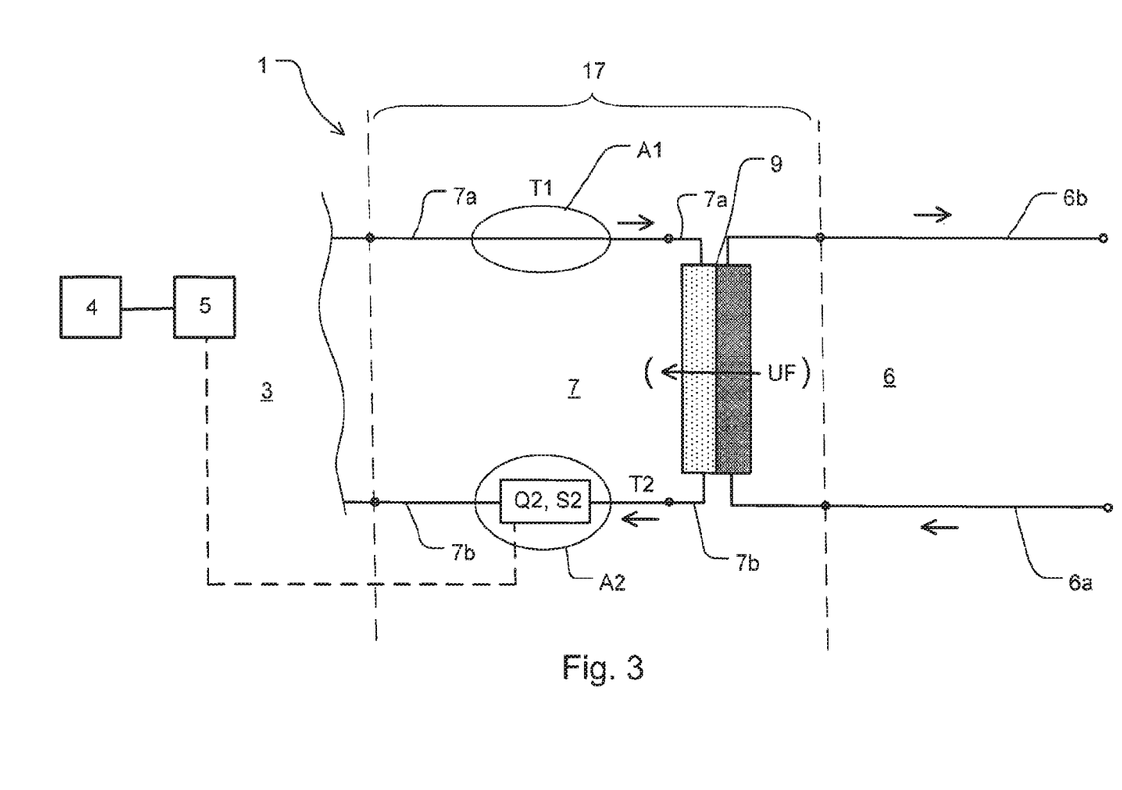
FIG. 3 shows, in a highly simplified illustration, an exemplary arrangement of a treatment apparatus having a further functional device.

The temperature T1 may be determined by means of a purely optionally provided or intended temperature sensor S1. As can be seen in FIG. 3, this temperature S1 is however not required when the temperature T1 is known or may be estimated.

The temperature T2 may be determined by means of an also purely optionally provided or intended temperature sensor S2. This temperature sensor S2 is however not required, in particular when the temperature T2 is known or may be estimated. For example, it may be assumed, in some particular treatment scenarios, in sufficiently good approximation that T2 corresponds to the body temperature of the patient.

The fluid circuit 1 may comprise a device for detecting the temperature difference between the first and the second section instead of the temperature sensor S1 and/or of the temperature sensor S2.

As suggested in FIG. 2 by the dashed lines, the sensors Q1, Q2, S1, S2 are preferably in signal communication with the control or the regulating devices 5.

FIG. 3 being based, as well as the following figures, on FIG. 1 and FIG. 2, shows, in a highly simplified illustration, a functional device 17 in another exemplary embodiment.

The functional device 17 corresponds substantially to that of FIG. 2. However, unlike the embodiment of FIG. 2, here no temperature sensor S1 is provided for measuring the temperature T1. In any case, the temperature T1 is not measured by a temperature sensor S1. The temperature sensor S1 is rather unnecessary when the temperature T1 is known or is estimated. For example, in some particular treatment scenarios, it can be assumed in sufficiently good approximation, that T1, the temperature with which the fluid flows through the first section A1, corresponds to the temperature the fluid has in a fluid source that supplies the fluid line 7a.

It should further be noted that in certain embodiments, the temperature sensor S2 for measuring the temperature T2 is not strictly necessary. That is, the temperature T2 need not be measured in each case by a temperature sensor S2. In fact, used dialysate shows or has for example a low temperature variation when flowing out of the filter device 9. Generally, the temperature of the fluid flowing out from the filter device 9 varies within the range of the body temperature (ca. 37° C.), so that therefore, it may be provided or intended to determine only the temperature of the fluid flowing into the first section A1 or not to determine any temperature at all (but rather to assume this temperature) in order to determine the temperature difference (DT) between sections A1 and A2.

FIG. 3 shows further that also the first flow sensor Q1 may be unnecessary. This is can be the case when the first flow F1 is known or may be estimated. This may for example be the case if at least the first volume flow F1 or the second volume flow F2 is adjustable and/or set, in particular by a device suitable for this purpose, e.g. a pump and/or a control or regulating device and/or an input device.

The particular feature of the embodiment of FIG. 3, according to which there is no necessity of a flow sensor Q1 and/or of a temperature sensor S1 for the first section and/or of a temperature sensor S2 for the second section A2, is combinable, where useful, with any other embodiment described herein.

Figure 4:
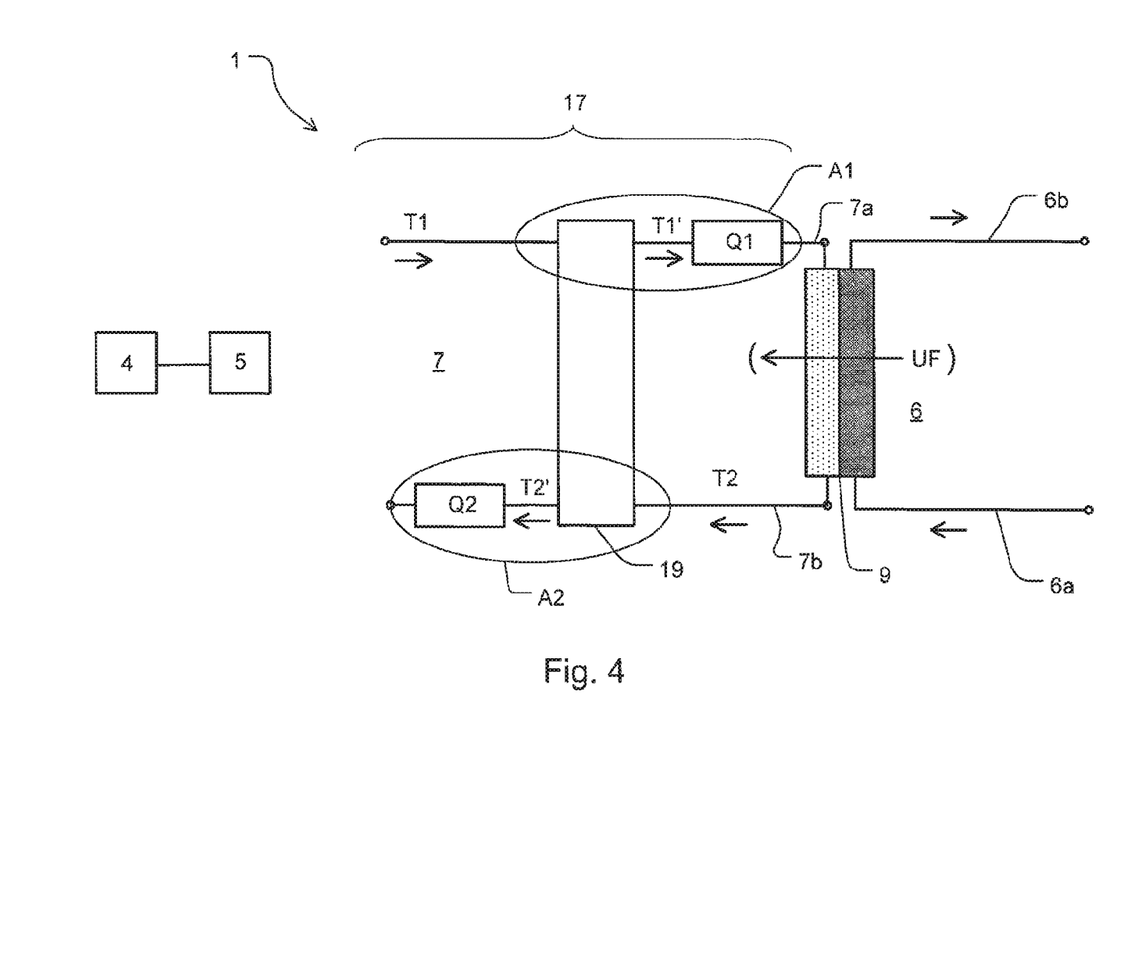
FIG. 4 shows, in a highly simplified illustration, a further functional device.

FIG. 4 shows in a highly simplified illustration a further embodiment of the functional device 17.

The functional device 17 comprises, optionally, a first and a second flow sensor Q1 and Q2. It comprises further at least one heat exchange device 19 or is connected thereto.

The optionally provided first flow sensor Q1 is arranged in a first section A1 of the substituate or dialysate circuit 7 of the fluid circuit 1, preferably in the dialysis fluid line 7a. The optionally provided second flow sensor Q2 is arranged in a second section A2 of the substituate or dialysate circuit 7 of the fluid circuit 1, preferably in the dialysate line 7b.

The first section A1 is purely optionally positioned upstream of a filter device 9 (for example a blood filter), the second section A2 is purely optionally positioned downstream of the filter device 9. In this example, the first and the second sections A1, A2, are optionally each in fluid communication with the filter device 9.

The heat exchange device 19 is arranged with regard to the flow direction of the fluid during a blood treatment (said directions being indicated by arrows) for an exchange of heat or thermal energy between the fluid flowing through the first section A1 and the fluid flowing through the second section A2.

In particular, the heat exchange device 19 is optionally arranged upstream of the first flow sensor Q1, which is itself arranged upstream of the filter device 9. The heat exchange device 19 is at the same time optionally arranged upstream of the second flow sensor Q2, which is again arranged downstream of the filter device 9.

The heat exchange device 19 may optionally be part of the first and/or the second section A1, A2, in particular an integral part thereof, and/or it may optionally only be connected, in particular thermally, with the first and/or with the second section A1, A2.

The heat exchange device 19 is provided, suitable and/or designed to effect a heat exchange and preferably even a heat balance or compensation, between the fluid flowing through the first section A1 and the fluid flowing through the second section A2.

A heat balance may mean that the difference between a temperature T1' of the fluid leaving the heat exchange device 19 but before entering the first flow sensor Q1, and in particular before entering the filter device 9, and a temperature T2' of the fluid flowing out after passing the heat exchange device 19 but before entering the second flow sensor Q2, is zero or substantially zero. The expression heat balance may also be understood as that the above-mentioned difference is in any case less than the difference between the temperature T1 and T2, which the fluid or fluids respectively had before entering the heat exchange device 19.

Even if the embodiment of FIG. 4 does not require a temperature sensor, it is optionally additionally provided or intended to detect the temperature T1 and/or the temperature T2, for example by at least one temperature sensor (not illustrated) and/or to set or adjust the temperature T1 and/or the temperature T2, in particular by means of a suitable device such as a heater.

Figure 5:
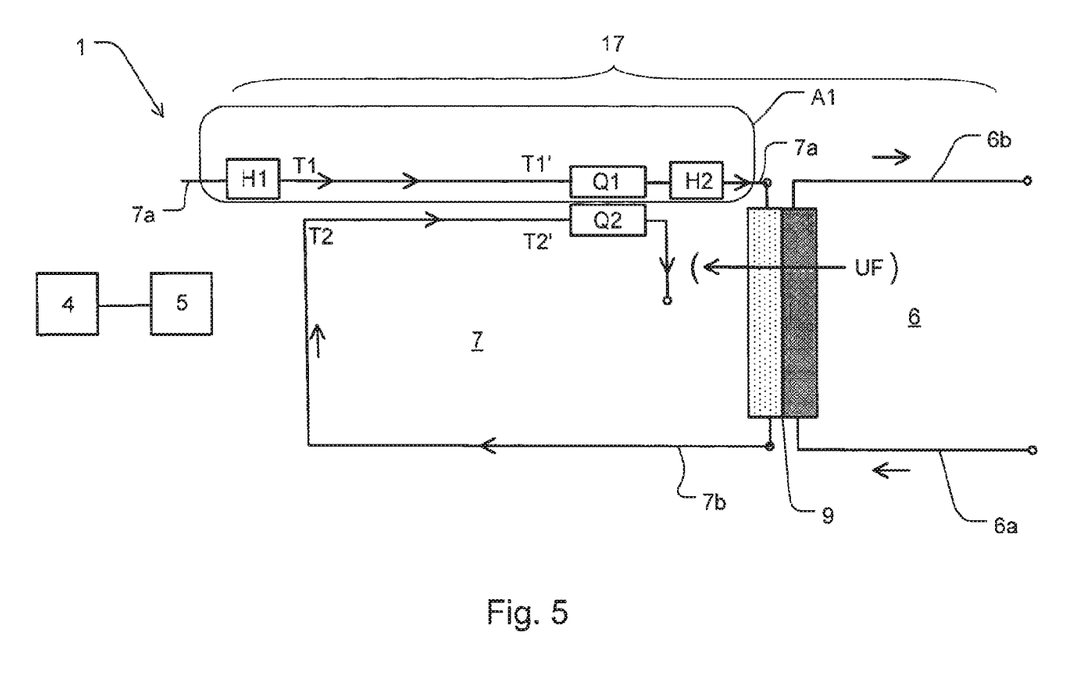
FIG. 5 shows, in a highly simplified illustration, yet a further functional device.

FIG. 5 shows, in a highly simplified illustration, another example embodiment of the functional device 17. In this example, the arrangement and/or embodiment of the functional device 17 may additionally comprise at least one heater Hi (i=1,2).

The heater Hi may in particular be arranged in the first section A1 of the fluid circuit 1. There are two heaters H1 and H2 illustrated in the shown example. Both are exemplarily arranged and/or embodied in the first section A1. The first heater H1 is arranged, by way of example, upstream or before the flow sensor Q1, while the second heater H2, by way of example, is arranged downstream or after the flow sensor Q1. Both heaters H1, H2 are, purely exemplarily, not part of the functional device 17.

Some embodiment include only one heater H1 or H2, or include further heaters (additional to heaters H1 and H2) in the fluid circuit 1.

Also, at least one heater Hi, in particular in a first section A1 of the fluid circuit 1, may be arranged upstream or before a heat exchange device 19 and/or downstream or after a flow sensor (not illustrated), which is itself arranged downstream or after the heat exchange device.

In a further, not illustrated embodiment of the functional device 17, a heater Hi may, purely optionally, be designed and/or arranged at, in and/or at least in connection with the heat exchange device 19 (FIG. 4).

The heater may be designed to facilitate or ensure a predetermined temperature of the fluid. Thus, a measurement of temperature may advantageously be unnecessary in certain embodiments.

Heaters, as shown in FIG. 5, may be of course combined with the arrangements of the embodiments shown in the preceding figures.

Using the arrangements of the figures and the particular configuration of the balancing unit 4, a correct fluid balance FB can be generated. Alternatively or additionally, a corrected ultrafiltration rate UF korr may be generated.

Hereinafter, certain aspects shall be further described by the following examples and partly with reference to the figures discussed above. The following examples are, like all numerical values give in the examples, purely exemplary and do not limit the present invention.

In the first section A1 (see for example FIG. 2) a fluid which may—purely exemplary—be a dialysis fluid that enters with T1=20° C. The first sensor Q1 measures a flow F1 of 200 ml/min.

In the second section A2, a dialysate flows with T2=37° C. There at section A2, the second sensor Q2 measures a flow F2 of 200 ml/min.

Temperature-dependent errors, caused for example by a density difference of the fluid and/or volume difference of the fluid at the two flow sensors Q1, Q2, which are due to the temperature difference of the fluid between A1 and A2, may contribute in a circuit (e.g., the fluid circuit 7) up to 0.5% or more of the measuring results (here the flow F1 or F2). In such an exemplary case, for example 60 ml/h fluid not withdrawn from the patient may be unnoticed.

The method advantageously allows such temperature-dependent measurement errors, which may in particular be geometrical (i.e. changes in the lumen of the tubing and others) and/or density errors, for example as described below, to be considered and/or compensated for.

EXAMPLE 1:

In some embodiments, the temperature difference DT (i.e. the difference between the temperature T1 and T2 which the fluid has at both measuring sites or points S1 or S2 in the first section A1 or second section A2, respectively) is determined to facilitate compensation for temperature-dependent measurement errors.

When the temperature difference DT is known, the measured volume flow value, here for example the flow or volume flow F2 being measured by means of the second flow sensor Q2, may be corrected by calculation. Thereby, the correction by calculation may take place proportionally to the temperature difference and/or to a factor K, here for example, K=0.000294/C. (per Celsius degree).

The factor K may be determined experimentally and/or theoretically and, for example, may be stored in a table. Similarly, the correction value may be stored in a table.

The temperature difference DT is determined, in this example, to be:

$$DT=T2-T1=(37-20)° C.=17° C.$$

The corrected value of the second flow sensor may be calculated from Formula 3' as follows:

$$F2\_korr=F2*(1+K*DT)=200*(1+0.000294*17)=201 \text{ ml/min}.$$

In this example, the measured volume flow value F2 can now be replaced by the second flow value F_korr. This correction, which leads to an increase of 1 ml/min of the further mathematically used measuring value of the second flow sensor Q2, allows the fluid balance FB to be balanced through changing a treatment parameter (such that it is zero or its deviation is below a predetermined threshold). An intervention in the controlling of the treatment apparatus is not required in this example, but can be carried out as shown in Example 2.

EXAMPLE 2:

Based on a system as is already described in Example 1, a filter device 9 as illustrated in FIG. 2 is additionally assumed. It is controlled or triggered to effect, for example, an ultrafiltration rate (UF) of 500 ml/h.

As in Example 1, the temperature-dependent measurement error, in particular the density error, is of about 0.5% of the fluid flow in the scale.

Without compensation of the temperature-dependent error and with the values of the preceding Example 1, there would therefore be, through the filter device, an effective ultrafiltration rate of 440 ml/h instead of the desired ultrafiltration rate (UF) of 500 ml/h.

A corrected ultrafiltration rate (UF_korr), which is to be set, may be determined based on the temperature difference (DT) between the two volume flows as follows:

$$UF\_korr=UF+F1*K+DT=500 \text{ ml/h}+(200 \text{ ml/h}*0.000294*17)=560 \text{ ml/h}.$$

The corrected ultrafiltration rate UF korr may be communicated or transmitted and/or used for controlling and/or regulating a control and/or regulating device, for example an ultrafiltration pump.

LIST OF REFERENCE NUMERALS 1 fluid circuit
3 treatment apparatus
4 balancing unit
5 control and regulating device
6 blood circuit
6a arterial blood line
6b venous blood line
7 dialysate and/or substituate circuit 7a dialysis fluid line
7b dialysate line
9 filter device
15 first pump
16 second pump
17 functional device
19 heat exchange device
A1 first section of the dialysate and/or substituate circuit
A2 second section of the dialysate and/or substituate circuit
Q1 first flow sensor
Q2 second flow sensor
S1 temperature sensor
S2 temperature sensor
F1 first volume flow in the first section of the fluid circuit
F2 second volume flow in the second section of the fluid circuit
T1 first temperature in at least one first section of the fluid circuit
T1' first temperature in at least one first section of the fluid circuit after passing through the heat exchange device
T2 second temperature in at least one second section of the fluid circuit
T2' second temperature in at least one second section of the fluid circuit after passing through the heat exchange device
T temperature in at least one section of the fluid circuit

The invention claimed is:

1. A method for determining a fluid balance between fluid flows in a fluid circuit of a medical functional device that does not comprise a balancing chamber, the method comprising:
measuring, using a first magnetic-inductive flow sensor positioned within a first section of the fluid circuit, a first fluid volume flow in the first section of the fluid circuit towards a filter device, wherein the first section is directly coupled to the filter device;
measuring, within the first section, a first fluid temperature of fluid flowing through the first section of the fluid circuit towards the filter device;
measuring, using a second magnetic-inductive flow sensor positioned within a second section of the fluid circuit downstream of the filter device, a second fluid volume flow in the second section of the fluid circuit away from the filter device;

determining, within the second section, a second fluid temperature of fluid flowing through the second section of the fluid circuit and away from the filter device;

determining a temperature difference between the first fluid temperature and the second fluid temperature;

determining a corrected value of the second fluid volume flow based on the second fluid volume flow determined using the second magnetic-inductive flow sensor and (i) the determined second fluid temperature or (ii) the determined temperature difference;

determining the fluid balance based on the first fluid volume flow and the corrected value of the second fluid volume flow; and controlling or regulating at least one of the first fluid volume flow or the second fluid volume flow by controlling at least one of: (i) a heater, or (ii) a cross-section of at least one section of the fluid circuit, wherein the controlling is based on at least one of: the fluid balance, the corrected value of the second fluid volume flow, the second fluid temperature, or the temperature difference.

2. The method according to claim 1, wherein the corrected value of the second fluid volume flow takes is based on a stored, temperature-dependent, physical quantity of the fluid in the fluid circuit, or a predetermined factor K, or both.

3. A balancing unit configured to determine a fluid balance between a first fluid volume flow in a first section of a fluid circuit and a second fluid volume flow in a second section of the fluid circuit, the balancing unit comprising:

a functional device comprising the fluid circuit, wherein the functional device does not comprise a balancing chamber;

a first temperature sensor arranged in the first section;

a second temperature sensor arranged in the second section; and a controller configured to execute a method comprising:

measuring, using a first magnetic-inductive flow sensor positioned within the first section of the fluid circuit, the first fluid volume flow in the first section of the fluid circuit towards a filter device, wherein the first section is directly coupled to the filter device;

measuring, within the first section, a first fluid temperature of fluid flowing through the first section of the fluid circuit towards the filter device;

measuring, using a second magnetic-inductive flow sensor positioned within the second section of the fluid circuit downstream of the filter device, the second fluid volume flow in the second section of the fluid circuit away from the filter device;

determining, within the second section, a second fluid temperature of fluid flowing through the second section of the fluid circuit and away from the filter device;

determining a temperature difference between the first fluid temperature and the second fluid temperature;

determining a corrected value of the second fluid volume flow based on the second fluid volume flow determined using the second magnetic-inductive flow sensor and (i) the determined second fluid temperature or (ii) the determined temperature difference;

determining the fluid balance based on the first fluid volume flow and the corrected value of the second fluid volume flow; and controlling or regulating at least one of the first fluid volume flow or the second fluid volume flow by controlling at least one of: (i) a heater, or (ii) a cross-section of at least one section of the fluid circuit, wherein the controlling is based on at least one of: the fluid balance, the corrected value of the second fluid volume flow, the second fluid temperature, or the temperature difference.

4. The balancing unit according to claim 3, wherein the controller is in data communication with at least one of: the first temperature sensor, the second temperature sensor, and at least one volume flow sensor of the functional device.

5. The balancing unit according to claim 3, wherein the controller is configured to control a volume flow of the fluid circuit.

6. A medical treatment apparatus, comprising:

a balancing unit configured to determine a fluid balance between a first volume flow in a first section of a fluid circuit and a second volume flow in a second section of the fluid circuit, the balancing unit comprising:

a functional device comprising the fluid circuit, wherein the functional device does not comprise any balancing chamber;

a first temperature sensor arranged in the first section;

a second temperature sensor arranged in the second section; and a controller; wherein the controller is configured to execute a method comprising:

measuring, using a first magnetic-inductive flow sensor positioned within the first section of the fluid circuit, a first fluid volume flow in a first section of the fluid circuit towards a filter device, wherein the first section is directly coupled to the filter device;

measuring, within the first section, a first fluid temperature of fluid flowing through the first section of the fluid circuit towards the filter device;

measuring, using a second magnetic-inductive flow sensor positioned within the second section of the fluid circuit downstream of the filter device, a second fluid volume flow in a second section of the fluid circuit away from the filter device;

determining, within the second section, a second fluid temperature of fluid flowing through the second section of the fluid circuit and away from the filter device;

determining a temperature difference between the first fluid temperature and the second fluid temperature;

determining a corrected value of the second fluid volume flow based on the second fluid volume flow determined using the second magnetic-inductive flow sensor and (i) the determined second fluid temperature or (ii) the determined temperature difference;

determining the fluid balance based on the first fluid volume flow and the corrected value of the second fluid volume flow; and controlling or regulating at least one of the first fluid volume flow or the second fluid volume flow by controlling at least one of: (i) a heater, or (ii) a cross-section of at least one section of the fluid circuit, wherein the controlling is based on at least one of: the fluid balance, the corrected value of the second fluid volume flow, the second fluid temperature, or the temperature difference.

7. A digital storage medium with electrically readable control signals that when executing by one or more processors causes one or more devices to carry out operations comprising:
- measuring, using a first magnetic-inductive flow sensor positioned within a first section of a fluid circuit of a functional device that does not comprise a balancing chamber, a first fluid volume flow in the first section of the fluid circuit towards a filter device, wherein the first section is directly coupled to the filter device;
- measuring, within the first section, a first fluid temperature of fluid flowing through the first section of the fluid circuit towards the filter device;
- measuring, using a second magnetic-inductive flow sensor positioned within a second section of the fluid circuit downstream of the filter device, a second fluid volume flow in the second section of the fluid circuit away from the filter device;
- determining, within the second section, a second fluid temperature of fluid flowing through the second section of the fluid circuit and away from the filter device;
- determining a corrected value of the second fluid volume flow based on the second fluid volume flow determined using the second magnetic-inductive flow sensor and (i) the determined second fluid temperature or (ii) a temperature difference between the determined first fluid temperature and the determined second fluid temperature;
- determining a fluid balance based on the first fluid volume flow and the corrected value of the second fluid volume flow; and
- controlling or regulating at least one of the first fluid volume flow or the second fluid volume flow by controlling at least one of: (i) a heater, or (ii) a cross-section of at least one section of the fluid circuit,
- wherein the controlling is based on at least one of: the fluid balance, the corrected value of the second fluid volume flow, the second fluid temperature, or the temperature difference.

* * * * *